United States Patent [19]

Heckele

[11] Patent Number: 4,517,962

[45] Date of Patent: May 21, 1985

[54] NASAL ENDOSCOPES

[75] Inventor: Helmut Heckele, Knittlingen, Fed. Rep. of Germany

[73] Assignee: Richard Wolf GmbH, Knittlingen, Fed. Rep. of Germany

[21] Appl. No.: 448,808

[22] Filed: Dec. 10, 1982

[30] Foreign Application Priority Data

Dec. 11, 1981 [DE] Fed. Rep. of Germany ... 8136066[U]

[51] Int. Cl.³ .............................................. A61B 1/06
[52] U.S. Cl. ........................................ 128/6; 433/80
[58] Field of Search ........................................ 128/4–8, 128/11, 66, 303.1, 399–402; 433/85, 100, 80

[56] References Cited

U.S. PATENT DOCUMENTS 2,691,370 10/1954 Wallace .................................... 128/6
4,412,823 11/1983 Sakai et al. ............................. 128/66

FOREIGN PATENT DOCUMENTS 169174 of 1961 U.S.S.R. ..................................... 128/6

Primary Examiner—Edward M. Coven
Assistant Examiner—Max F. Hindenburg
Attorney, Agent, or Firm—Hill, Van Santen, Steadman & Simpson

[57] ABSTRACT

This invention relates to an endoscope for endonasal surgery for which different optical systems are required. With this invention it is possible to exchange an optical system and/or a matching flushing and suction shaft as desired while still utilizing the same endoscope shaft handle and without requiring the interchange of the complete endoscope including its handle. To accommodate this function, the handle including flushing and suction passages can be mated with interchangeable flushing and suction shafts and a desired optical system. Such shafts and optical system are releasably connected to the endoscope handle.

2 Claims, 3 Drawing Figures

NASAL ENDOSCOPES

BACKGROUND OF THE INVENTION

The present invention relates to an endoscope for endonasal surgery comprising a handle traversed by a flushing and suction passage and carrying a flushing and suction shaft and an optical system extending through said shaft.

In known endoscopes of the aforesaid nature, the suction and flushing shaft was rigidly connected to the handle. Endoscopic surgery however requires inspection of a large portion of the nasal sinuses and of the ethmoid bone area, which cannot be surveyed with a single optical system, so that it was necessary to bring different optical systems into use, which however required a matching flushing and suction passage of different form at the distal end of the instrument. A matching flushing and suction shaft and accordingly with it also the handle to which the shaft had been rigidly secured, consequently also had to be exchanged for the different optical systems.

It is an object of the invention to provide means whereby an exhange of the optical system and of the matching flushing and suction shaft may be performed rapidly and easily under retention of one and the same handle.

SUMMARY OF THE INVENTION

Accordingly, to achieve this and other objects, the invention consists in an endoscope for nasal surgery, having a handle traversed by a flushing and suction passage and carrying a flushing and suction shaft, and an optical system extending through said shaft, wherein said handle is provided with a coupling for interchange of different flushing and suction shafts each having an optical system, said flushing and suction shafts being connectable to said passages extending through said handle.

Advantageously, provision is made for the coupling to comprise a sleeve firmly joined to the handle and having a tapered recess at the proximal side for engagement of a matching tapered portion of the replaceable shaft and a delimiting stop inwardly directed at the distal end for a sliding support displaceable in the proximal direction within the sleeve against a spring means bearing on the sleeve. The sliding support may also have radial bores for receiving locking balls which prevent the withdrawal of the shaft out of the coupling sleeve and which after displacing the sliding support against a spring means may fall back in an outward radial direction into an internal annular recess.

It is possible thereby to free a unit consisting of an optical system and a flushing and suction shaft by releasing the coupling from the handle and to replace the same with another unit having a different optical system and a matching flushing and suction shaft in uncomplicated manner. This exchange of the units may easily be performed by displacing the sliding support manually in the proximal direction so that the locking balls may fall back radially outwards and the unit consisting of a flushing and suction passage and of an optical system may be withdrawn freely from the coupling and replaced by another unit.

BRIEF DESCRIPTION OF THE DRAWINGS

In order that the invention may be more clearly understood, reference will now be made to the accompanying drawings which show one particular embodiment thereof by way of example and in which.

DETAILED DESCRIPTION OF THE PREFERRED EMBODIMENT

Figure 1:
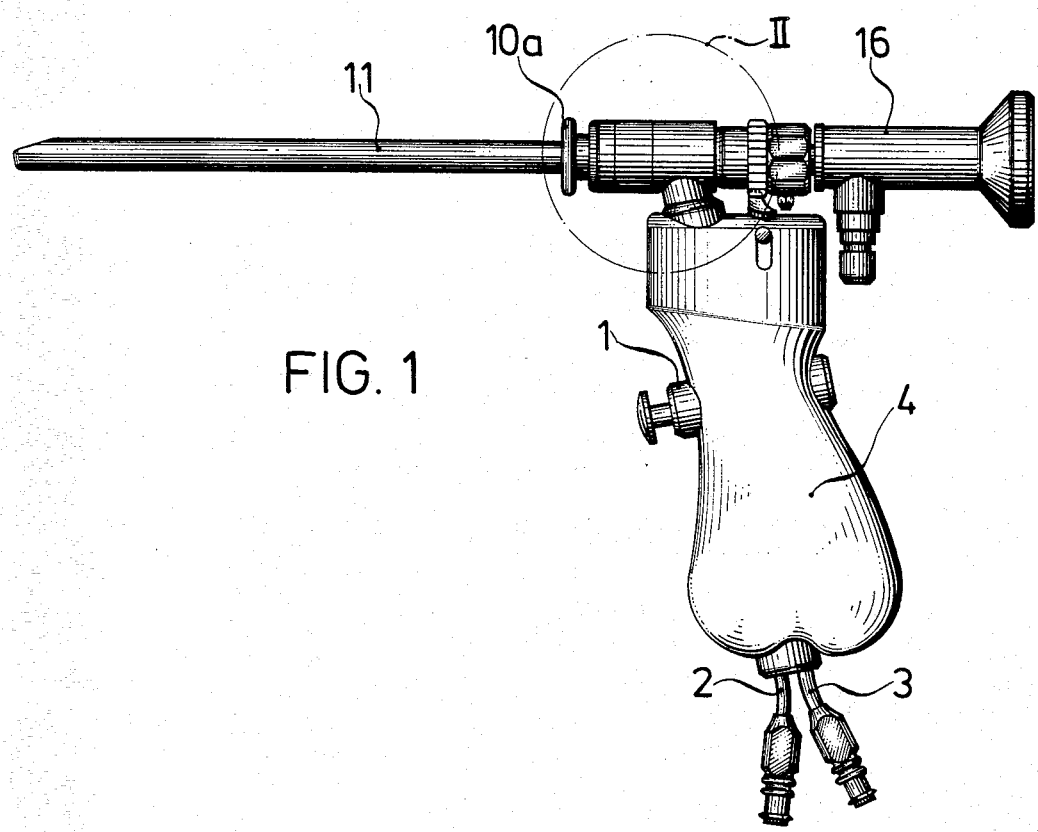
FIG. 1 is a side elevational view of an endoscope utilized for endonasal surgery.
Figure 2:
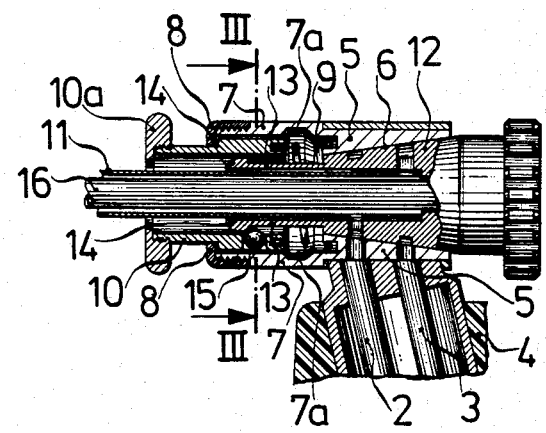
FIG. 2 is a fragmentary vertical sectional view (showing some parts in side elevation) of that portion of the endoscope of FIG. 1 indicated by the circle II in FIG. 1.
Figure 3:
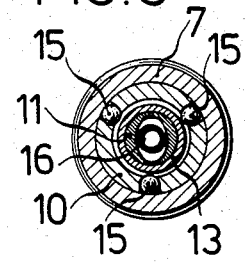
FIG. 3 is a vertical sectional view taken along the line III of FIG. 2.

Referring now to the drawings, the endoscope depicted is provided with a handle 4 through which pass flushing and suction passages 2 and 3 respectively, which are closable by means of a valve 1. (See particularly FIG. 2). The passages 2 and 3 open into annular grooves of a coupling sleeve 5 firmly joined to the handle which is part of a quick disconnect coupling means. The quick disconnect coupling means further includes a sleeve 5 is provided in the sleeve 5 a tapered recess 6 at the proximal end and at the distal end has a substantially cylindrical section 7 whose own distal extremity carries an inwardly directed delimiting stop 8 for a sliding support 10 which is axially displaceable within the section 7 against a spring 9 bearing on the sleeve 5, and which comprises an operating grip 10a. A flushing shaft 11 has secured thereto a tapered portion 12 which matches and is insertable into the tapered recess 6 of the coupling sleeve 5. In this embodiment, the tapered suction portion 12 has a cylindrical extension 13 at its distal end, terminating in an external delimiting stop 14.

The sliding support 10 has radial bores for the reception of locking balls 15 which may bear against the proximal side of the delimiting stop 14 and the sleeve section 7 is provided with an internal recess 7a into which the locking balls 15 may fall back.

To couple a flushing and suction shaft 11 having an optical system 16 and extending therethrough, to the handle 4, the sliding support 10 is displaced in the proximal direction against its spring means 9, so far that the locking balls 15 may fall back into the recesses 7a. The shaft 11, together with the optical system 16 which could however also be passed through the shaft later, is then led through the coupling sleeve 5 until the mating taper 12 is placed in engagement in the tapered recess 6. The thrust on the sliding support 10 is then neutralized, so that it is displaced in the distal direction by the spring means, until the locking balls 15 come into contact with the delimiting stop 14, the unit consisting of the shaft 11 and the optical system 16 thereby being coupled to the handle 4.

Conversely, the unit consisting of the shaft 11 and optical system 16 may be withdrawn from the coupling sleeve by displacing the sliding support 10 in the proximal direction, and may then be replaced by a different unit.

It may be advantageous to form the surface of the contact of the stop 14 for the locking balls 15 with an inclination from the inside towards the outside and towards the distal side, to enhance the locking action.

Although other modifications and changes may be suggested by those skilled in the art, it is the intention of the inventor to embody within the patent warranted hereon all changes and modifications as reasonably and properly come within the scope of his contribution to the art.

I claim:

1. An endoscope for endonasal surgery, having a handle with a distal and a proximal end, said handle traversed by flushing and suction passages and carrying a projecting flushing and suction shaft extending from said distal end of said handle, an optical system extending through said shaft, wherein said handle is provided with a quick disconnect coupling means for interchanging from said proximal end of said handle one of a plurality of different flushing and suction shafts each having an optical system associated therewith, said flushing and suction shafts each having complimentary coupling means mating with said quick disconnect coupling means, said flushing and suction shaft being in fluid-tight communication with said passages extending through said handle when said handle and said flushing and said suction shaft are connected by said coupling means.

2. An endoscope according to claim 1, wherein said quick disconnect coupling means and said complimentary coupling means comprise a sleeve firmly joined to said handle and having a tapered recess at its proximal end for engagement of a matching tapered portion of said replaceable shaft and a delimiting stop inwardly directed at the distal end for a sliding support displaceable in the proximal direction within said sleeve against a spring means bearing on said sleeve, said sliding support having radial bores to receive locking balls which prevent the withdrawal of said shaft out of said coupling sleeve and which, after displacing said sliding support against its spring means may fall back in outward radial direction into an internal annular recess.

* * * * *